United States Patent
Hamilton

(10) Patent No.: US 9,381,265 B2
(45) Date of Patent: *Jul. 5, 2016

(54) APPARATUS AND PROCESS FOR STERILIZATION AND PRESERVATION OF OBJECTS

(71) Applicant: Timothy F. Hamilton, Griffin, GA (US)

(72) Inventor: Timothy F. Hamilton, Griffin, GA (US)

(*) Notice: Subject to any disclaimer, the term of this patent is extended or adjusted under 35 U.S.C. 154(b) by 85 days.

This patent is subject to a terminal disclaimer.

(21) Appl. No.: 14/095,486

(22) Filed: Dec. 3, 2013

(65) Prior Publication Data

US 2014/0158909 A1 Jun. 12, 2014

Related U.S. Application Data

(63) Continuation-in-part of application No. 13/632,896, filed on Oct. 1, 2012, now abandoned, which is a continuation of application No. 12/062,221, filed on Apr. 3, 2008, now Pat. No. 8,278,628.

(60) Provisional application No. 60/909,811, filed on Apr. 3, 2007.

(51) Int. Cl.
*G01N 23/00* (2006.01)
*A61L 2/10* (2006.01)

(52) U.S. Cl.
CPC .................................... *A61L 2/10* (2013.01)

(58) Field of Classification Search
CPC ............ A61L 2/10; G01N 23/00; H01J 37/20
USPC .............. 250/455.11, 453.11; 422/22–24, 28, 422/116, 118, 186.3, 186.07
See application file for complete search history.

(56) References Cited

U.S. PATENT DOCUMENTS

| | | | |
|---|---|---|---|
| 5,527,508 A * | 6/1996 | Childers et al. ................. | 422/33 |
| 6,159,422 A | 12/2000 | Graves et al. | |
| 6,495,100 B1 * | 12/2002 | Lin et al. ......................... | 422/29 |
| 7,695,673 B2 | 4/2010 | Moisan et al. | |
| 8,278,628 B2 * | 10/2012 | Hamilton ................. | 250/455.11 |
| 2005/0074342 A1 * | 4/2005 | Lemme et al. ................ | 417/415 |
| 2005/0194026 A1 * | 9/2005 | Lu .................................. | 134/105 |

OTHER PUBLICATIONS

International Search Report and Written Opinion dated Mar. 23, 2015 in PCT/US2014/068136 which claims the benefit of U.S. Appl. No. 14/095,486.

* cited by examiner

*Primary Examiner* — David Porta
*Assistant Examiner* — Meenakshi Sahu
(74) *Attorney, Agent, or Firm* — Stephen J. Weyer, Esq.; Stites & Harbison, PLLC

(57) ABSTRACT

This apparatus and method improves the way metal and other objects will be sterilized, disinfected and preserved by utilizing both electromagnetic radiation (UV light in particular) to kill anaerobic pathogens and oxygen depletion to kill aerobic pathogens. The removal of the presence of oxygen further increases the useful lifespan of the treated object by preventing corrosion in general and oxidation in particular.

17 Claims, 3 Drawing Sheets

APPARATUS AND PROCESS FOR STERILIZATION AND PRESERVATION OF OBJECTS

CROSS-REFERENCE TO RELATED APPLICATIONS

This application is a continuation-in-part of U.S. patent application Ser. No. 13/632,896, filed Oct. 1, 2012, which claims the benefit of U.S. patent application Ser. No. 12/062,221 filed Apr. 3, 2008 and issued as U.S. Pat. No. 8,278,628 on Oct. 2, 2012; which in turn claims the benefit of U.S. Provisional Application No. 60/909,811, filed Apr. 3, 2007 (all hereby incorporated by reference).

BRIEF SUMMARY OF THE INVENTION

An improved apparatus and process for sterilization and preservation of objects is disclosed that can be used to disinfect, sterilize and preserve metal objects through the use of ultraviolet light. Although machines that sterilize metal objects through the use of ultraviolet light already exist, one preferred embodiment of the apparatus and process sterilizes metal using a new and novel apparatus and method, in which a vacuum is created that will remove all of the air and oxygen from the container containing the metal object that is to be sterilized with ultraviolet radiation. Optionally, the removed air can be replaced by an inert gas such as nitrogen. This process of removing air from the container and optionally replacing the air with inert gas has two advantages: 1) decreases the pathogenicity of aerobic flora and therefore aerobic pathogens will die in the absence of $O_2$ and the object will remain sterilized and 2) the metal object will not oxidize or rust.

DETAILED DESCRIPTION OF THE INVENTION

Figure 1:
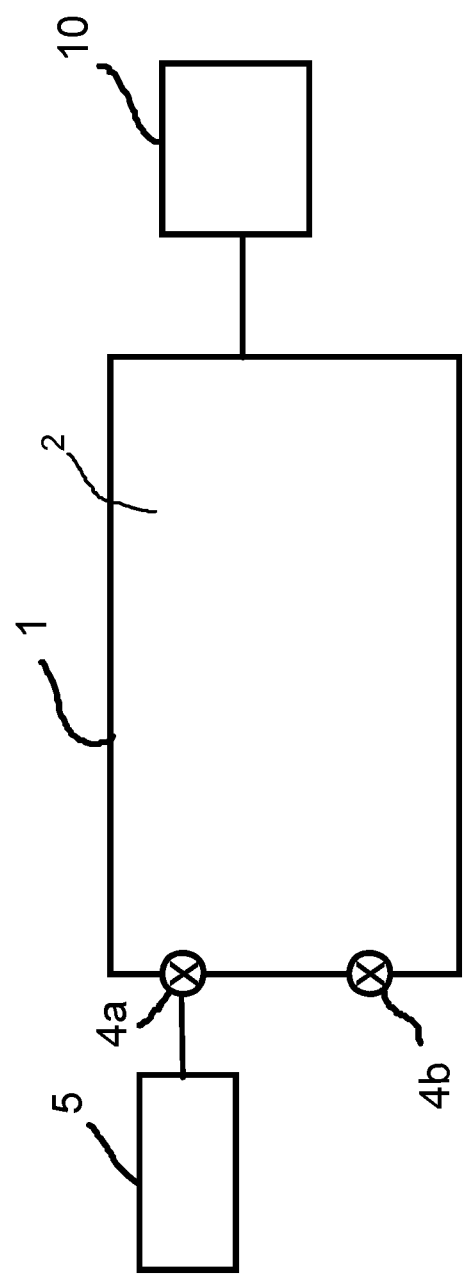
FIG. 1 is a schematic diagram showing a preferred embodiment of the present invention.
Figure 2:
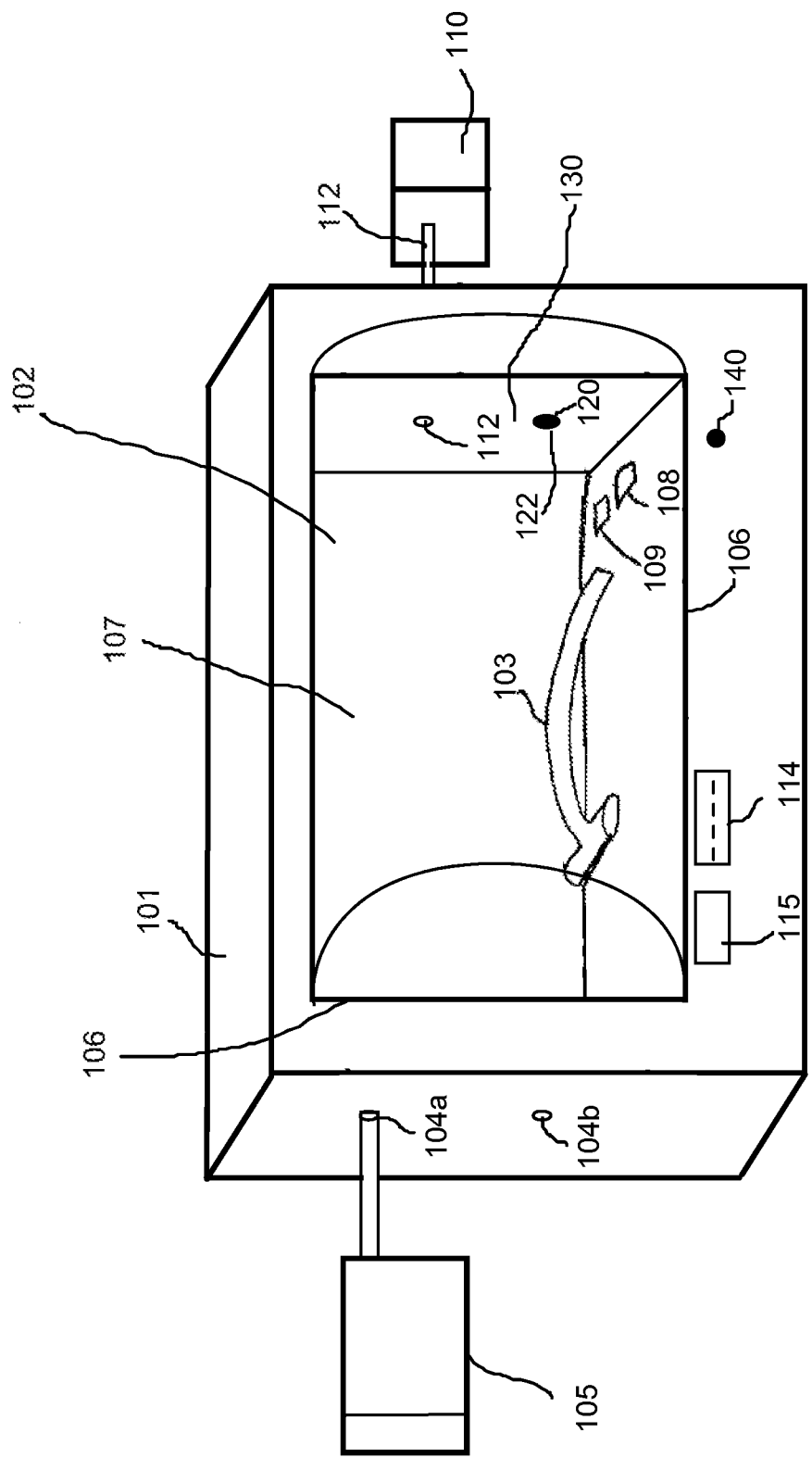
FIG. 2 is a drawing of a preferred embodiment of the present invention.

Referring now to the drawings where FIG. 1 is a schematic drawing of a general embodiment of the present invention and FIG. 2 is a further specific preferred embodiment, reference numbers in FIG. 2 which correspond to elements in FIG. 1 have been raised by 100. Only unique elements to FIG. 2 will be discussed separate from the elements in the general embodiment of FIG. 1.

The apparatus includes a canister 1 having a work chamber 2 into which the object 3 to be sterilized, disinfected and preserved is inserted and secured. The canister 1 will be a (preferably) clear material (including but not limited to glass, composite plastic, or metal). The canister 1 will be constructed in order to achieve and maintain an ideal vacuum. It will open sufficiently to allow emplacement of the target object. The canister 1 could be lined with a reflective material. Two airtight valves 4a and 4b will be incorporated into the apparatus 1 to allow the removal of air and the introduction of an inert gas (such as nitrogen) into the chamber 2. The source at the inert gas would be a separate tank or a gas generator 5. The exchange of gas for the vacuum will allow for reduction of pressure on the valve seals 4a and 4b (which will maintain structural integrity of the chamber 2 and the seals 6) and will allow for continued aerobic pathogenesis. The source of the nitrogen gas can be a tank or a nitrogen generator 5 that separates nitrogen gas from the air. The exchange of the gases will reduce the pressure on the airtight seals 6. Furthermore, it will ensure the cessation of oxidation and death of aerobic pathogens which need oxygen to survive.

The chamber 2 will include a compartment 7 which will be exposed to the vacuum. The chamber 2 will contain a dessilant 8 such as silica gel to remove $H_2O$. The chamber 2 also will contain an oxygen scavenger 9 to remove $O_2$.

The intensity of the electromagnetic radiation source 10 varies inversely with the square of the distance from the source. The electromagnetic radiation source 10 should in close proximity to the object 3 being exposed. The source of the electromagnetic radiation either inside of the canister 1 or outside of the canister 1. A cable 12 could be used to transmit the wavelengths of interest to the inside of the canister.

UV light will degrade plastic, therefore, the canister 1 should be made of a UV-resistant material that will not degrade as quickly.

Depending upon the scale of the target objects, the vacuum needed for atmospheric replacement may be done by a large electronic or smaller hand pump 5. There are several options for the production of a vacuum. For larger scale industrial use or hospital use, a large vacuum pump can be used. For residential use, a hand pump could be utilized.

A timer 14 will be incorporated with an on/off switch 15 to indicate the completion of the process and to control the electromagnetic radiation source. The user will have the option of keeping the sterilized and disinfected object in the canister, in the non-corrosive atmosphere until ready for use.

Figure 3B:
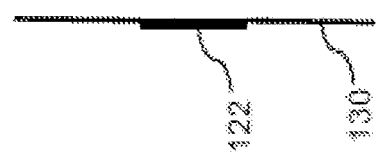
FIG. 3b is the vacuum indicator of FIG. 3a after a vacuum has been achieved.
Figure 3A:
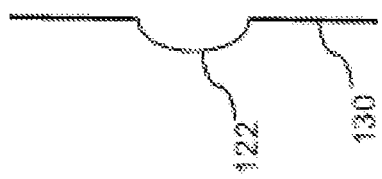
FIG. 3a is a cross-sectional view of a vacuum indicator shown in FIG. 2, prior to a vacuum being achieved in the canister

Advantageously, the present apparatus includes at least one indicator that indicates that a suitable vacuum has been achieved and is maintained within the compartment 107. An advantageous vacuum pressure is at least −14.7 psi although other vacuum pressures above and below this pressure may be desirable depending on the sterilization which include but is not limited to −5 to −20 psi. Vacuum indicator 120 comprises a flexible membrane 122. Prior to a sufficient vacuum being achieved in compartment 107, the membrane 122 lies substantially flat along an interior surface 130 of the chamber 107 (see e.g. FIG. 2 and FIG. 3a depicting the flexible membrane 122 in the canister 107 before a vacuum is achieved. After a sufficient vacuum is achieved, the flexible membrane 122 will be drawn into the compartment 107 as shown in FIG. 3b. The flexible membrane 122 is composed of an appropriate material and thickness so that it indicates when a desired vacuum is achieved. An additional vacuum indicator can be provided by illumination of vacuum indicator light 140. Once a desired pressure is achieved within compartment 107, the vacuum light indicator 140 is illuminated and stays illuminated as long as a desired sufficient pressure is maintained within compartment 107. For example, the apparatus can include a pressure sensitive switch that activates the vacuum indicator light 140 to indicate that a vacuum pressure has been achieved within compartment 107. The apparatus may include a feedback control loop logic circuit in order to maintain a constant vacuum pressure within the compartment 107. The feedback system would have a maximum and minimum boundaries in order to achieve a desired set point vacuum for maintaining a desired pressure within compartment 107.

What is claimed is:

1. An apparatus for sterilization and preservation of an object using electromagnetic radiation, comprising:
    a canister provided with an opening for insertion of an object;
    a vacuum-tight seal of the opening of the canister to thereby allow a vacuum to be created and maintained within the canister;
    a light source which generates electromagnetic radiation directed towards objects to be placed within said canister; and
    a device for removing air from inside the canister to thereby create a vacuum in the housing.

2. The apparatus of claim 1, wherein the device for removing air comprises a device for removing oxygen.

3. The apparatus of claim 1, wherein the light source generates UV light which is directed into the canister for sterilizing and preserving metal objects placed therein.

4. The apparatus of claim 3, wherein the light source generates an electromagnetic radiation sufficient to sterilize an object within the canister.

5. The apparatus of claim 1, further comprising a gas source for generating gas to be pumped into the canister.

6. The apparatus of claim 5, wherein the gas source generates an inert gas to be pumped into the canister.

7. The apparatus of claim 6, wherein the inert gas is nitrogen.

8. The apparatus of claim 1, wherein the canister is lined with reflective material.

9. The apparatus of claim 1, further comprises a vacuum indicator.

10. The apparatus of claim 9, wherein the vacuum indicator is a flexible membrane which deflects inward into the canister when a desired vacuum is achieved in the canister.

11. The apparatus of claim 9, wherein the vacuum indicator is a light which illuminates when a desired pressure is achieved within the canister.

12. The apparatus of claim 1, wherein the objects to be placed within the apparatus are metal objects.

13. The apparatus of claim 1, further comprising one or more objects within the canister.

14. The apparatus of claim 13, wherein at least one of the objects in the canister is a metal object.

15. The apparatus of claim 9, wherein the objects to be placed within the apparatus are metal objects.

16. The apparatus of claim 9, further comprising one or more objects within the canister.

17. The apparatus of claim 16, wherein at least one of the objects in the canister is a metal object.

* * * * *